United States Patent [19]
Hellberg et al.

[11] Patent Number: 5,691,360
[45] Date of Patent: Nov. 25, 1997

[54] COMPOUNDS HAVING BOTH POTENT CALCIUM ANTAGONIST AND ANTIOXIDANT ACTIVITY AND USE THEREOF AS CYTOPROTECTIVE AGENTS

[75] Inventors: Mark R. Hellberg; George Barnes; Robert J. Collier, Jr., all of Arlington, Tex.

[73] Assignee: Alcon Laboratories, Inc., Fort Worth, Tex.

[21] Appl. No.: 471,550

[22] Filed: Jun. 6, 1995

Related U.S. Application Data

[62] Division of Ser. No. 164,267, Dec. 8, 1993, Pat. No. 5,424,321.

[51] Int. Cl.$^6$ ............................................. A61K 31/44
[52] U.S. Cl. ................................. 514/337; 514/338
[58] Field of Search ............................ 514/337, 338

[56] References Cited

U.S. PATENT DOCUMENTS 4,550,022  10/1985  Garabedian et al. ............... 424/127

FOREIGN PATENT DOCUMENTS

| | | |
|---|---|---|
| 232025 | 12/1987 | European Pat. Off. . |
| 0 267 155 | 5/1988 | European Pat. Off. . |
| 164247 | 11/1988 | European Pat. Off. . |
| 424901 | 2/1991 | European Pat. Off. . |
| 460418 | 11/1991 | European Pat. Off. . |
| WO 89/05803 | 6/1989 | WIPO . |

OTHER PUBLICATIONS

Peruche, et al., "Mechanisms Of Drug Actions Against Neuronal Damage Caused By Ischemia—An Overview", *Prog. Neuro–Psychopharmacol. and Biol. Psychiat.*, vol. 17, pp. 21–70 (1993).

Miller, R., "Multiple Calcium Channels and Neuronal Function", *Science*, vol. 235, pp. 46–52 (1987).

Triggle, et al., "Ca$^+$ Channel Ligands: Structure–Function Relationships of The 1,4–Dihydropyridines", *Medicinal Research Reviews*, vol. 9, No. 2, pp. 123–180 (1989).

Sahly, et al., "Calcium channel blockers inhibit retinal degeneration in the retinal-degeneration-B mutant of *Drosophila*", *Proc. Natl. Acad. Sci. USA*, vol. 89, pp. 435–439 (1992).

Beck, et al., "Local cerebral glucose utilization and local cerebral blood flow in conscious rats after administration of flunarizine", *Naunyn–Schmiedeberg's Arch Pharmacol*, vol. 335, pp. 680–685 (1987).

Aruoma, et al., "Free Radical Scavenging And Inhibition Of Lipid Peroxidation By β–Blockers And By Agents That Interfere With Calcium Metabolism", *Biochemical Pharmacology*, vol. 42(4), pp. 735–743 (1991).

Orrenius, et al., "Calcium Ions and Oxidative Cell Injury", *Annals of Neurology*, supplement to vol. 32, pp. ξ33–42 (1992).

Jackson, et al., "Antioxidants: A Biological Defense Mechanism for the Prevention of Atherosclerosis", *Medicinal Research Reviews*, vol. 13, No. 2, pp. 161–182 (1993).

Li, et al., "Amelioration of Retinal Photic Injury by a Combination of Flunarizine and Dimethylthiourea", *Experimental Eye Research*, vol. 56, pp. 71–78 (1993).

Kubo, et al., "Radical Scavenging Action of Flunarizine in Rat Brain in vitro", *Arch. int. Pharmacodyn.*, vol. 272, pp. 283–295 (1984).

Mak, et al., "Comparative Antioxidant Activities of Propranolol, Nifedipine, Verapamil, and Diltiazem Against Sarcolemmal Membrane Lipid Peroxidation", *Circulation Research*, vol. 66, No. 5, pp. 1449–1452 (1990).

Breugnot, C., et al., "Calcium Antagonists Prevent Monocyte And Endothelial Cell–Induced Modification Of Low Density Lipoproteins", *Free Rad. Res. Comms.*, vol. 15, No. 2, pp. 91–100 (1991).

Zimmerman, J., et al., "In Vitro Modulation Of Human Neutrophil Superoxide Anion Generation By Various Calcium Channel Antagonists Used In Ischemia–Reperfusion Resuscitation", *Biochemical Pharacology*, vol. 38, No. 20, pp. 3601–3610 (1989).

Ehlert, F., et al., "The Binding Of [$^3$H]Nitrendipine To Receptors For Calcium Channel Antagonists In The Heart, Cerebral Cortex, And Ileum Of Rats", *Life Science*, vol. 30, pp. 2191–2202 (1982).

Lamba, O., et al., "Spectroscopic detection of lipid peroxidation products and structural changes in a sphingomyelin model system", *Biochimieu et Biophysica Acta.*, 1081, pp. 181–187 (1991).

Gould, R., et al., "[$^3$H]Nitrendipine–labeled calcium channels discriminate inorganic calcium agonists and antagonists", *Proc. Natl. Acad. Sci. USA*, vol. 79, pp. 3656–3660 (1982).

Scheschonka, A, et al., "Temporal Relationships Between The Loss Of Vitamin E, Protein Sulfhydryls And Lipid Peroxidation In Microsomes Challenged With Different Prooxidants", *Chem.–Biol. Interactions*, vol. 74, pp. 233–252 (1990).

Shanklin Jr., J., et al., "Synthesis, Calcium–Channel–Blocking Activity, and Antihypertensive Activity of 4–(Diarylmethyl)–1–[3–(aryloxy)propyl]piperidines and Structurally Related Compounds", *Journal of Medicinal Chemistry*, vol. 34, No. 10, pp. 3011–3022 (1991).

Barrett, R., et al., "AHR–16303B, a Novel Antagonist of 5–HT$_2$ Receptors and Voltage–Sensitive Calcium Channels", *Journal of Cardiovascular Pharmacology*, vol. 17, No. 1, pp. 41–53 (1991).

Cross et al., *Annals of Internal Medicine*, 1987, 107: 526–545.

Diplock et al., *Annals of The New York Academy of Science*, vol. 570, pp. 4–5 (1989).

Oyanagui, Y., "Antioxidant and O$_2$–production inhibitory effects of calcium–antagonists", *Chemical Abstracts*, vol. 117:40025c, No. 5, p. 45, col. 2 (1992).

*Primary Examiner*—Jane Fan
*Attorney, Agent, or Firm*—James A. Arno; Gregg C. Brown

[57] ABSTRACT

Compounds having both calcium antagonist and antioxidant activity are disclosed. The compounds are useful in preventing or alleviating damage to tissues at the cellular level. Methods of treatment which employ these properties of the compounds and corresponding pharmaceutical compositions are also disclosed.

5 Claims, No Drawings

COMPOUNDS HAVING BOTH POTENT CALCIUM ANTAGONIST AND ANTIOXIDANT ACTIVITY AND USE THEREOF AS CYTOPROTECTIVE AGENTS

This is a Division of application Ser. No. 08/164,267, filed Dec. 8, 1993 now U.S. Pat. No. 5,424,321.

BACKGROUND of the INVENTION

1. Field of the Invention

The present invention is directed to the provision of compounds having potent calcium antagonist and antioxidant activity, and to the use of those compounds as cellular protective agents. The invention is further directed to the provision of methods for synthesizing the compounds of the invention and to compounds formed as intermediates during the synthesis. The invention is particularly directed to the use of the compounds of the present invention to prevent or reduce cellular damage associated with ophthalmic diseases or injuries.

2. Discussion of Related Art

In a biological system under stress induced by trauma, ischemia-reperfusion, depletion of natural defenses, inflammation, light damage (especially laser or intense operating room light), or degenerative conditions, damage occurs which can result in an increase in cellular free calcium and/or an increase in oxidative damage. Both these changes are components of the common pathway of cell death. The result of these changes is the initiation of a cascade of cellular destruction, loss of cellular function and ultimately cell loss. The loss of critical cellular components can result in organ damage and loss of organ function. Loss of function can be caused by an acute insult or may be the result of the cumulative effects of chronic insult. The following texts may be referred to for further details concerning these phenomena:

Prog. Neuro-Psychopharmacol. and Biol. Pysch., volume 17, pages 21–70 (1993);

Age, volume 16, pages 23–30 (1993);

Chem. Res. Tox., volume 32, pages 2–18 (1993); and

Ann. Neurol., volume 32, pages S33–42 (1992).

Calcium flux is a necessary part of normal cell function. The level of intracellular free calcium is highly regulated. Both receptor-operated and voltage-sensitive channels control cell signaling and stimulus response. Multiple voltage-sensitive calcium channels have been identified. These include the N, T, P, and L channels. The following publications may be referred to for further background concerning the regulation of intracellular free calcium levels:

Med. Res. Review, volume 9, pages 123–80 (1989);

Pharmacol. Review, volume 38(4), pages 321–416 (1986);

Cardiovasc. Drugs and Therapy, volume 6, pages 35–39 (1992);

Science, volume 235, pages 46–52 (1987);

Chem.-Biol. Interactions, pages 1–23 (1991); and

Biochemical Pharmacol., volume 43(1), pages 39–46 (1992).

Over-stimulation of the cell or cellular system or the defective regulation of intracellular free calcium can result in increased intracellular free calcium levels. This can lead to the initiation of a chain of biochemical processes which can lead to cell death. Agents that modulate increases in intracellular free calcium concentration can moderate the deleterious effects of over-stimulation or defective regulation. See PNAS, volume 89, pages 435–39 (1992), and references cited above. In addition, a compound that acts as a calcium antagonist can provide an additional beneficial effect by improving blood flow, reducing ischemic insult and facilitating repair. See Naunyn-Schmiedeberg's Acta Pharmacol, volume 335, pages 680–685 (1987). As utilized herein, the term "calcium antagonists" refers to organic molecules which inhibit increases in intracellular free calcium concentrations.

Agents that act as antioxidants can protect against oxidative damage associated with cellular stress. Such protection has been the subject of numerous scientific publications, including the following:

Arch. Pharmacol., volume 325, pages 129–146 (1992);

Free Rad. Biol. Med., volume 6, pages 209–224;

Free Rad. Biol. Med., volume 11, pages 215–232 (1991);

Ear. J. Pharmacol., volume 210, pages 85–90 (1992);

J. Photochem., Photobiol. Biol., volume 8, pages 211–224 (1991);

Pharmacol. and Tox., volume 70, pages 271–277 (1992); and

Medicinal Res. Rev., volume 13(2), pages 161–182 (1993).

The combined use of two or more compounds having calcium antagonist and antioxidant activity, respectively, is discussed in Experimental Eye Research, volume 5, pages 71–78 (1993). The provision of compounds having both calcium antagonist and antioxidant activity is discussed in the following patent publications: EP 267 155A and WO 89/05803 A1.

One compound known to have calcium antagonist activity, flunarizine, has also been reported to have free radical scavenging activity. See:

Arch. int. Pharmacodyn., volume 272, pages 283–295 (1984);

Eur. J. Pharmocol., volume 204, pages 315–322 (1991); and

Meth. and Find Exp. Clin. Pharmacol., volume 11(10), pages 607–612 (1989).

In addition, other classes of calcium antagonists have been reported to have antioxidant activity. See:

Free Rad. Biol. and Med., volume 12, pages 183–187 (1992);

Res. Commun. in Chem. Path. and Pharnacol., volume 76(3), pages 367–370 (1992);

J. Mol. Cell Cardiol., volume 22, pages 1199–1208 (1990);

Circulation Res., volume 66(5), pages 1449–1452 (1990);

J. Caxdiovas. Pharmacol, volume 18(Suppl. 1) pages S6–S10 (1991);

Basic Res. in Cantiology, volume 87, pages 148–160 (1992);

Free Rad. Res. Comres, volume 15(2), pages 91–1130 (1991); and

Biochem. Pharmacol, volume 37(21), page 4197 (1988).

However, in most cases the antioxidant effect reported is weak and not clinically relevant. This is pointed out in Biochem. Pharmacol, volume 42(4), pages 735–743 (1991), and Biochem. Pharmacol, 38(20), pages 3601–3610 (1989).

In addition, it is believed that a number of the effects attributed to the free radical scavenging effect of flunarizine might actually be an effect of its calcium antagonist activity since this activity was poorly understood in the early 1980's.

The present invention is directed to the provision of new compounds that have both potent calcium antagonist and potent antioxidant activity in a single molecule. The use of a single chemical entity with potent antioxidant and potent calcium antagonist activity provides increased protection relative to the use of a compound with singular activity. The advantage of a single agent with both activities over a combination of two components would be realized by the uniform delivery of an active molecule simplifying issues of drug metabolism and delivery.

SUMMARY OF THE INVENTION

The present invention provides new compounds having potent calcium antagonist and antioxidant activity. The dual therapeutic action of the compounds provides a distinct advantage over prior therapies. The dual therapeutic actions act in a complementary manner to prevent or reduce cellular damage.

The compounds of the present invention are effective cytoprotective agents. These compounds were conceived by making modifications in known calcium antagonists which confer antioxidant activity while maintaining calcium antagonist activity. More specifically, the invention is based in part on the discovery of appropriate structural modifications of compounds having calcium antagonist activity which maintain the calcium antagonist activity of the compounds while adding potent antioxidant activity. By taking advantage of the limited allowed substitution in the dihydropyridine ring of known calcium antagonists, modifications can be made to instill potent antioxidant activity while retaining calcium antagonist activity.

The compounds and associated pharmaceutical compositions of the present invention may be used to prevent or alleviate damage to various types of tissues. However, the use of the compounds to prevent or reduce damage to ophthalmic tissues at the cellular level is a particularly significant aspect of the present invention. Conditions which may be treated include cataracts, retinopathies, heredodegenerative diseases, macular degeneration, ocular ischemia, neovascular diseases, glaucoma, and damage associated with injuries to ophthalmic tissues, such as ischemia reperfusion injuries, photochemical injuries, and injuries associated with ocular surgery, particularly injuries to the retina, cornea or other tissues caused by exposure to light or surgical instruments.

The compounds of the present invention are capable of protecting against cellular damage caused by a wide range of insults. Since the compounds provide this protection by decreasing free radical or oxidative damage and by reducing the increase in intracellular free calcium, it represents a two-prong approach to cytoprotection. Both of these mechanisms are responsible for the loss of cellular viability associated with stress regardless of the source. In addition, the expected increase in blood flow due to the calcium antagonist activity contributes to the therapeutic effect. Among other things, the advantage of a single compound over a combination of two or more compounds is that the single entity offers uniform delivery of an active molecule having both antioxidant and calcium antagonist properties. The use of a single compound rather than a combination of compounds greatly simplifies issues of pharmacokinetics, drug metabolism, and delivery.

DETAILED DESCRIPTION OF THE INVENTION

The compounds of the present invention have the following formula:

wherein:

A is an antioxidant;

R is $C_1$ to $C_6$ alkyl, straight chain or branched;

n is a whole number of from 1 to 6;

m is a whole number of from 1 to 6;

Z is O or NH;

Y, if present, is O or $S(O)_{n'}$, and n' is 0, 1 or 2; and

B is selected from:

wherein:

$R^1$ and $R^2$ are the same or different and are selected from H, I Br, Cl, F, $CF_3$, CN, $NO_2$ and $S(O)_{n'}$.

The most preferred compounds are those wherein: R is methyl; m is a whole number from 1 to 4; Z is O; Y is O or is absent; and, if one of $R^1$ or $R^2$ is H, then the other $R^1$ and $R^2$ must be Cl, $CF_3$ or $NO_2$. Compounds wherein $R^1$ is in the 3 position and $R^2$ is in the 2 position are preferred. Compounds wherein both $R^1$ and $R^2$ are Cl are also preferred.

The following groups, wherein R has the same meaning as described above, are representative examples of the groups which may be utilized as the antioxidant moiety of the compounds of formula (I) and formula (II):

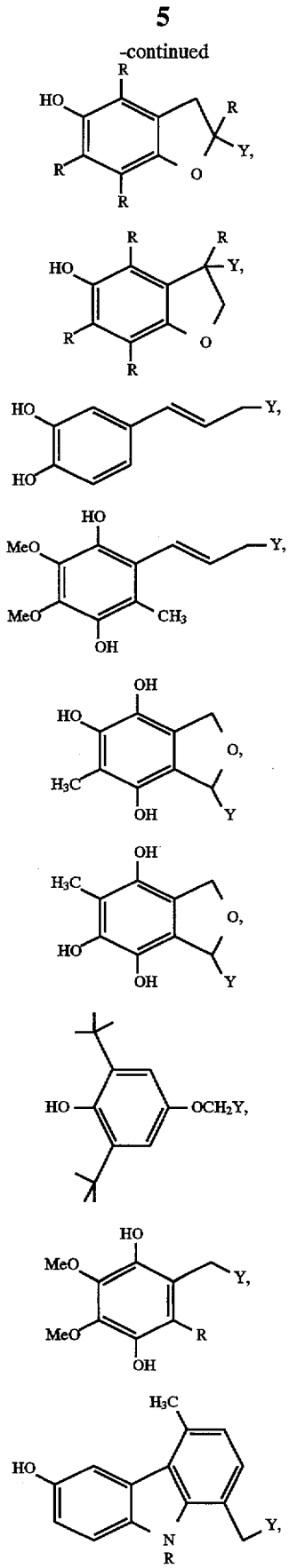

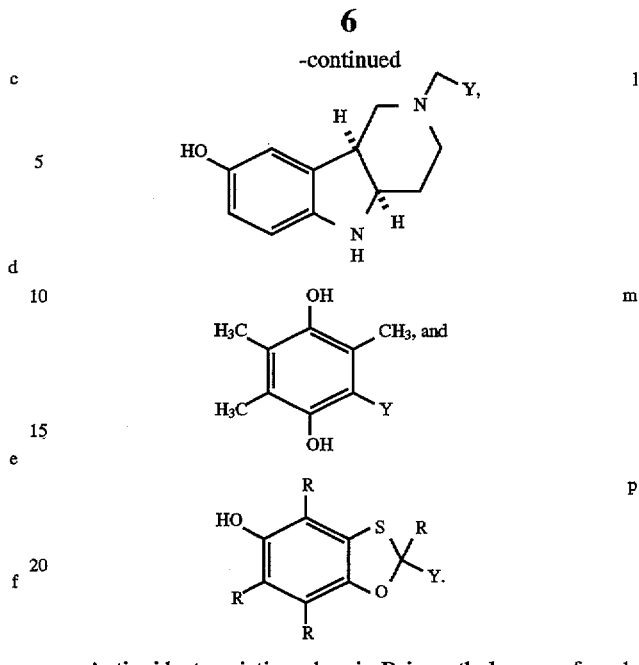

Antioxidant moieties wherein R is methyl are preferred. antioxidant moieties are:

Criteria for selecting specific antioxidant moieties and for evaluating antioxidant and calcium antagonist activity in relation to compounds of formula (I) and formula (II) are described below.

The antioxidant moieties of the above-described compounds are substances such as an organic molecule, which are known to be capable of reacting with the free radicals encountered in physiological systems. For a substance to have a protective effect as an antioxidant in a physiological system, it must act to prevent the damaging activity of free radicals by: (i) inhibiting the process leading to their generation, (ii) suppressing the amplification of the process by scavenging primary free radicals, or (iii) inhibiting the amplification of free radical-initiated damage by intercepting secondary free radicals. The thearapeutic activity of an antioxidant in a biological system depends on the source and nature of the damaging free radical, the site of damage, and the delivery of a therapeutically effective concentration of the antioxidant to the appropriate site. This invention is concerned with substances that demonstrate antioxidant activity by reacting with free radicals to reduce the damage caused by these species. The antioxidant component contributes to the cytoprotective activity of these compounds by quenching the primary free radicals or the free radicals generated as the primary damage process is amplified.

The preferred antioxidant moieties in the compounds of formula (I) and formula (II) are phenolic compounds. The antioxidant activity of these compounds is thought to reside in their ability to react with flee radicals and therefore terminate radical chain reactions. The reaction of these phenolic compounds with peroxyl free radicals in biological systems is particularly important. The phenoxyl radicals formed by the reaction of a free radical with a phenol are resonance stabilized and typically do not continue the chain reaction. In biological systems, the parent phenol from phenolic antioxidants such as α-tocopherol (vitamin E) can be regenerated from the phenoxyl free radical by vitamin C and/or glutathione (GSH), thereby providing a way to complete the detoxification process. See *Free Radical Biology & Medicine*, volume 15, pages 311–328 (1993).

The antioxidant activity of the phenolic compounds is enhanced by stabilizing the phenoxyl flee radical or by facilitating the transfer of the free radical to other components of the detoxification mechanism, such as GSH or vitamin C. Alkyl substituents stabilize the phenoxyl free radical by electron donation and the stearic bulk of ortho substituents reduces the propensity of the phenoxyl radical to participate in free radical chain reactions. An increase in stearic bulk from ortho dimethyl to ortho di-tert-butyl groups decreases the reactivity due to the excessive crowding of the reactive phenolic hydroxyl groups. In addition, overcrowding reduces the rate of exchange with the biological detoxification mechanisms, thereby reducing the efficiency of the antioxidant. The introduction of a parasubstituent such as an OH or O-alkyl group increases the stability of the phenoxyl free radical by delocalizing the electron density through p orbital overlap. By including the pan oxygen in a five or six membered ring, the p orbital of the oxygen is constrained in a position that approaches being perpendicular to the aromatic ring, providing near optimum overlap and allowing efficient delocaliation of the electron density. Combining ortho methylsubstituents with a para alkoxy group constrained in a five or six membered ring provides a phenolic compound with potent antioxidant activity. Antioxidant activity can be enhanced by selectively incorporating modifications such as those discussed above.

Based on the foregoing considerations and the known structure-activity relationships of the calcium antagonists, the above described phenolic groups are preferred as the antioxidant moiety of the present compounds. The most preferred antioxidant moieties are benzofuran and benzopyran derivatives, which provide potent antioxidant activity, but do not interfere with calcium antagonist activity.

The compounds of the present invention have free radical scavenging activity that can be measured by the ability of the above-described antioxidant moieties of the compounds to quench a stable free radical dye, such as 1,1'-diphenyl-2-picrylhydrazine (DPPH), as described in *Free Radical Research Communications*, volume 15, pages 91–100 (1991), or by the ability of the compound to protect against oxidative insult in liposomes or microsomes, as described in *Biochimica, Biophysica Acta*, volume 1081, pages 181–187 (1991) and *Chemical and Biological Interactions*, volume 74, pages 233–252 (1990), respectively. Thus, the antioxidant moieties in the compounds of the present invention will:

1) provide greater than 20% quench of the free radical at concentrations of DPPH and the test agent equal to $10^{-4}$M, in accordance with the above-cited DPPH assay;

2) demonstrate an $IC_{50}$ of less than 20 μM, in accordance with the above cited liposome assay; or 3) demonstrate an $IC_{50}$ of less than 20 μM, in accordance with the above-cited liver microsome assay.

Antioxidant moieties which satisfy the foregoing criteria are referred to herein as having "therapeutically significant free radical scavenging activity".

The calcium antagonist moieties of the compounds of the present invention are organic compounds which inhibit increases in intracellular-free calcium. Increased intracellular-free calcium may arise from the influx of calcium from extracellular sources or the release of sequestered calcium from intracellular stores. Intracellular-free calcium concentration is regulated by many mechanisms, including, for example, receptor-operated calcium channels, voltage-sensitive calcium channels, sodium-calcium exchangers, and calcium flux through sodium channels. A sustained increase in intracellular-free calcium results in events such as the deregulation of cellular metabolism and the activation of catabolic enzymes, such as calcium-activated proteases and phospholipases. This process can ultimately lead to cell loss. Calcium antagonism can inhibit the increase in intracellular calcium by various mechanisms including but not limited to:

a) preventing the flux through voltage-sensitive calcium channels (N,L,T,P);

b) blocking flux through receptor operated calcium channels;

c) preventing the release of calcium sequestered in sarcoplasmic reticulum; or d) blocking nonspecific channels (i.e., reversing sodium/calcium exchangers or blocking calcium flux through a sodium channel).

The compounds of the present invention act as calcium antagonists by inhibiting increases in intracellular calcium. The calcium antagonist activity of the compounds may be determined in accordance with one or more of the assays listed below:

1) radioligand binding assays, wherein radiolabeled nitrendipine is displaced from rat brain cortices (minimum activity: $IC_{50}$ of less than 20 μM), as described in *Life Scienee*, volume 30, pages 2191–2202 (1979) and *Procedures of the National Academy of Science, USA*, volume 79, pages 3656–3650 (1982);

2) calcium antagonist binding assays, such as the relaxation of pre-contracted rabbit aortic strips of greater than 7.0, as described in *Journal of Medicinal Chemistry*, volume 34, pages 3011–3022 (1991) and references cited therein (minimum activity: $IC_{50}$ value less than 20 μM);

3) inhibition of calcium flux in a cellular system, as measured by a fluorescent dye, in accordance with the procedures described in *Journal of Cardiovascular Pharmacology*, volume 17, pages 41–53 (1991), and references cited therein, (minimum activity: $IC_{50}$ of less than 100 nm); or 4) inhibition of calcium induced contractions of rabbit thoracic aortic strips, in accordance with the procedures described in *Journal Cardiovascular Pharmacology*, volume 17, pages 41–53 (1991), and references cited therein (minimum activity: $pA_2$ greater than 7).

Although the above-described activities define the upper limits for compounds expected to have cytoprotective activity afforded by the combined antioxidant/calcium antagonist mechanisms described herein, it is also necessary for the compounds to be delivered to the target tissue and for tissue levels to reach therapeutically effective levels, in order for the compounds to demonstrate cytoprotective activity. It is also to be understood that each of the compounds of formulas (I) and (II) is useful to different degrees for treating patients afflicted with or prone to various types of cellular damage. The success of treatment will depend on the type of cellular insult and the route of administration used to treat those conditions.

The compounds of formulas (I) and (II) may be prepared in accordance, with the general synthesis methods outlined in Schemes 1 and 2 below. More specific methods of synthesis are outlined in Schemes 3–5 below.

Scheme 1
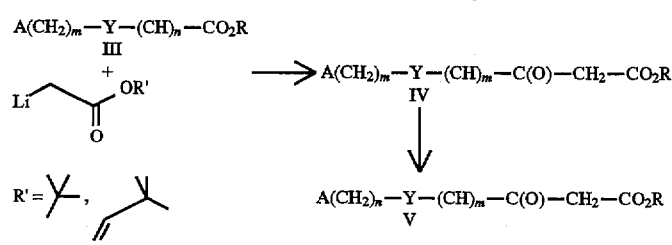
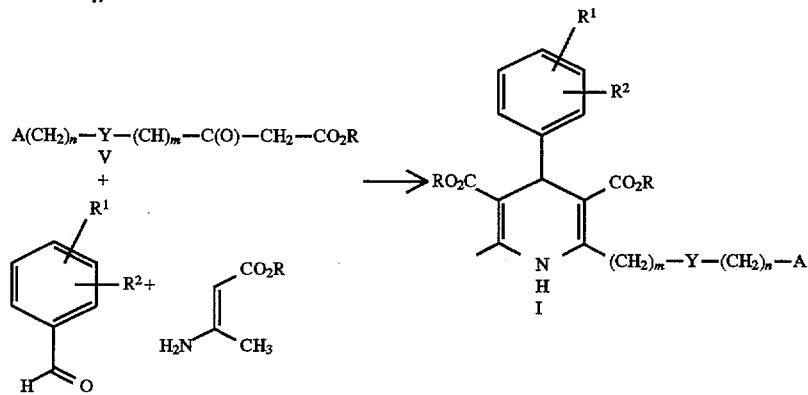
Scheme 2
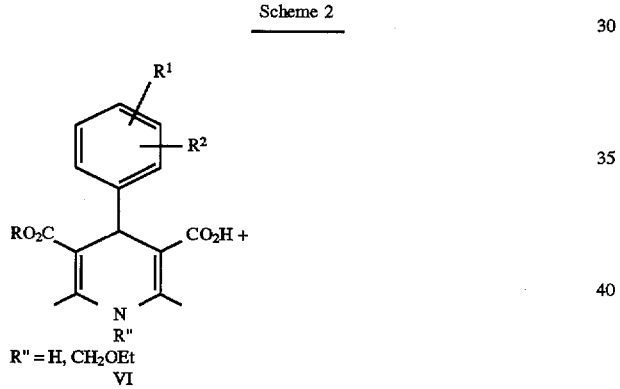
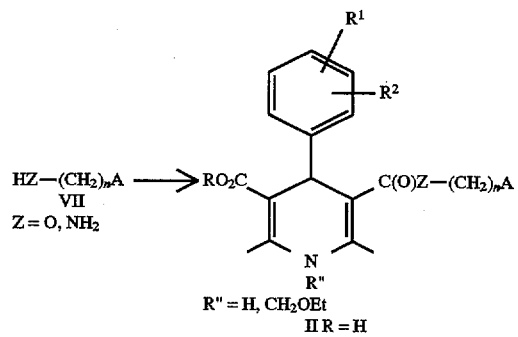
Scheme 3
Synthesis of VII
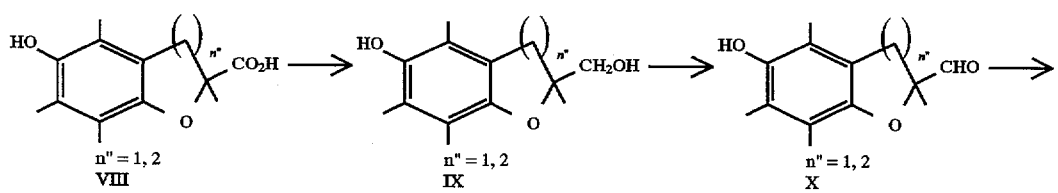

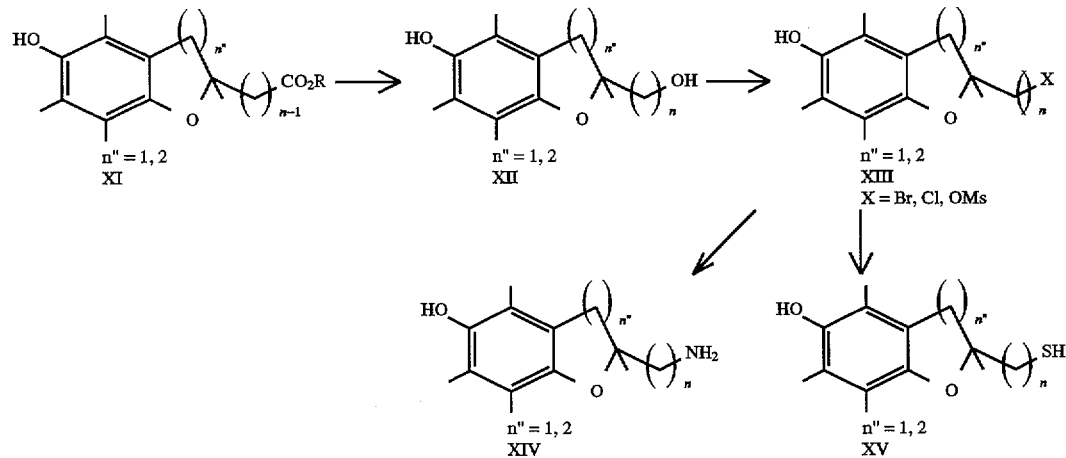
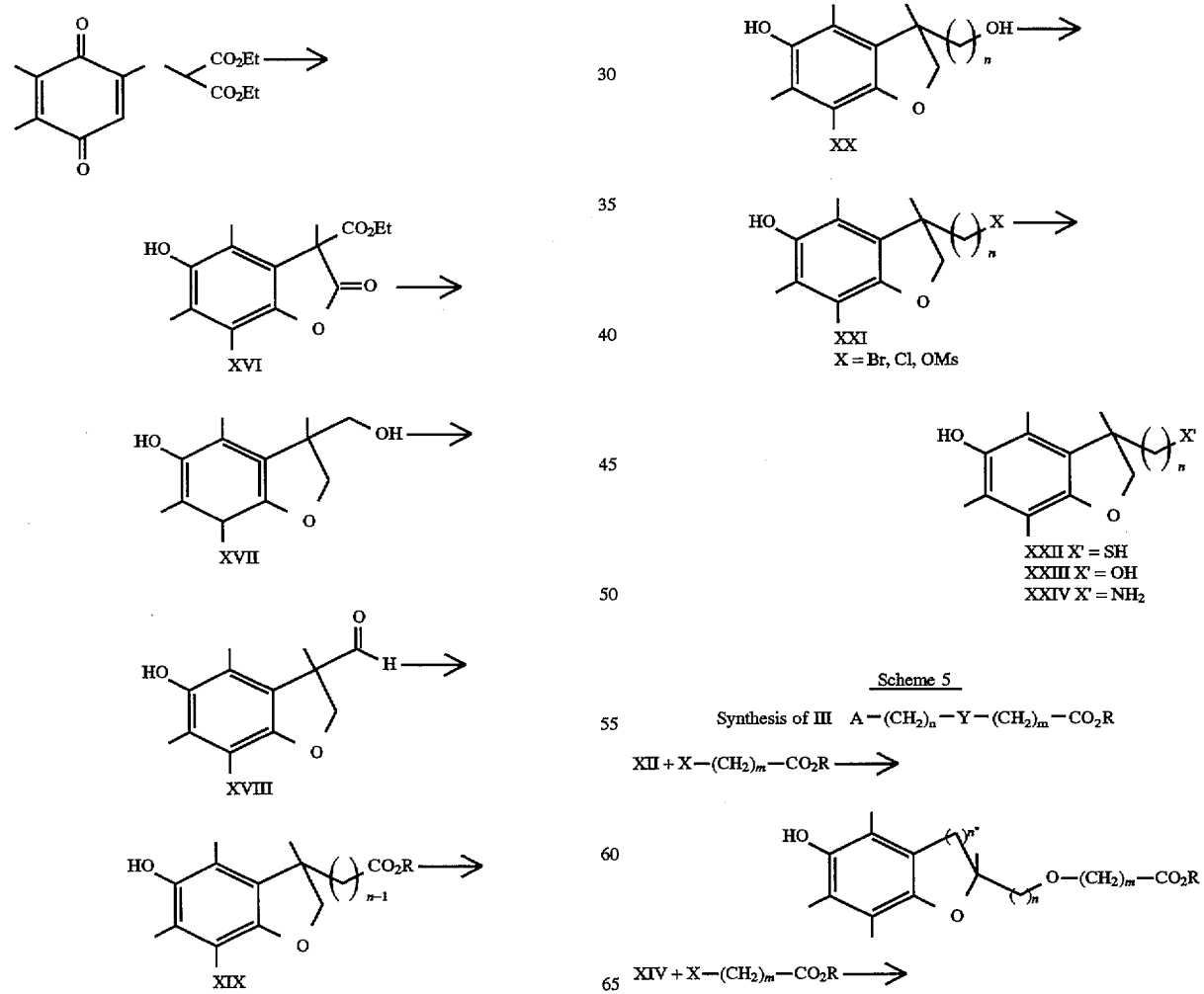
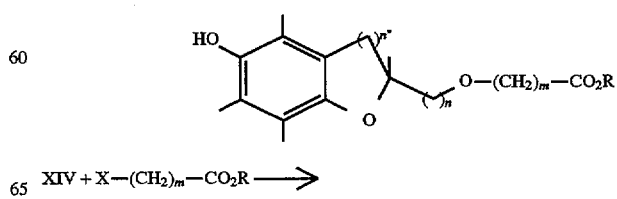

-continued
Scheme 5

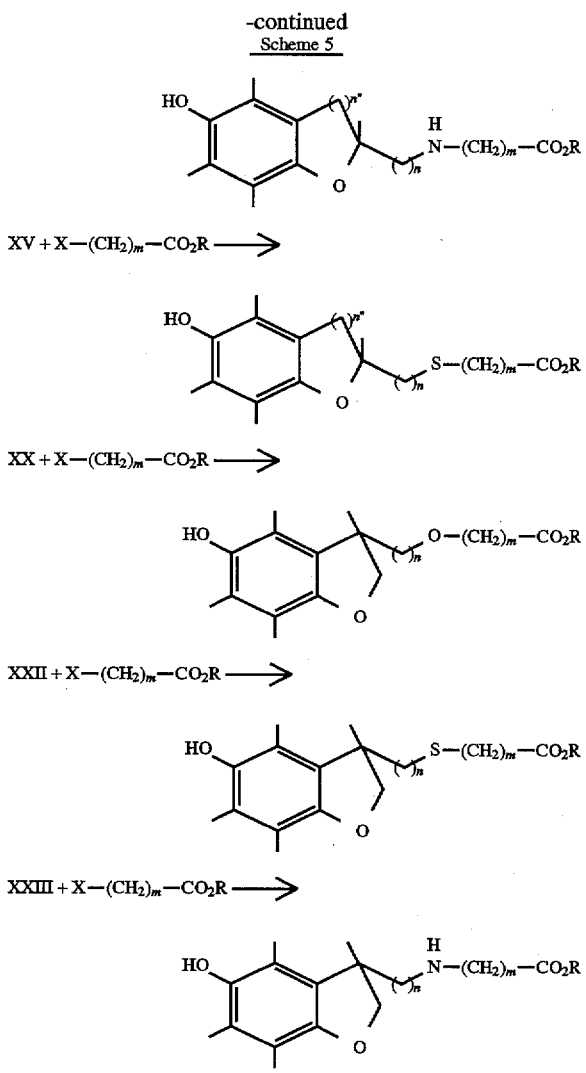

Compounds of structure I can be prepared in the following manner (Scheme 1). The ester, III, is convened into the 3-keto-ester, IV, by slowly adding a solution of the lithium salt of tert-butyl acetate to the ester, III, at temperatures between −78° C. and 23° C. (the preferred temperature being −78° C. and −50° C.) in an inert solvent, such as tetrahydrofuran, using the method described by Ohta (*Synthesis*, 1985, pages 45–47), or the method described by Yamaguchi, et al., in *Tetrahedron Letters*, volume 31, page 3913 (1990). The ester, IV, is isolated and then converted to the appropriate ester (V) by hydrolysis of the hindered ester, using acidic conditions, such as a 1:1 mixture of trifluoroacetic acid and methylene chloride. The resulting acid is then esterified using standard conditions. The methyl, ethyl and 2-propyl esters are the most preferred. The resulting keto-ester, V, can be converted to compound I using the general methods outlined by Arrowsmith, et al., in *Journal of Medicinal Chemistry*, volume 29, pages 1696–1702 (1986). The ester, V, is combined with the appropriate commercially available substituted benzaldehyde and stirred in a solvent, preferably ethanol or 2-propanol, at temperatures between 50° and 90° C. for a time between 15 minutes and 2 hours. To this mixture is added the appropriate aminocrotonate ester, preferably the methyl, ethyl or isopropyl ester, and acetic acid, and the resulting mixture is warmed at 50° C. to the reflux temperature of the solvent for 1 to 24 hours. The preferred conditions include warming at reflux in ethanol for 2.5 to 18 hours.

Compounds of formula II (Scheme 2) can be prepared by coupling the appropriate amine or alcohol, VII, to acid, V. Compound V was prepared using standard methods (see *Journal of Medicinal Chemistry*, volume 29, pages 2504–2511 (1986), and references cited therein). The acid, VI, can be converted to the acid chloride by adding thionyl chloride or phosphorus pentachloride to the acid in a solvent, such as methylene chloride, dimethyl formamide, acetonitrile or a mixture thereof (in the case of phosphorus pentachloride, the reaction is run neat) at temperatures maintained below 20° C. After stirring for 0.5 to 3 hours, a solution of the appropriate amine is added and the reaction mixture was allowed to stir at 0 to 50° C. for 3 to 24 hours. Alternately, the carboxylic acid, VI, can be coupled to the amine or alcohol using standard methods. The preferred methods involve using 1,3-dicyclohexylcarbodiimide or 1-(3-dimethylaminopropyl-3-ethylcarbodiimide and 1-hydroxy-benzotriazole or 4-dimethylaminopyridine in a solvent such as dimethylformamide, methylene chloride or acetonitrile or a mixture thereof. If the compound is protected as the ethoxymethyl derivative, the protecting group is removed by mild acid hydrolysis, such as dilute hydrochloric acid in acetone.

The esters of the general formula III (see Scheme 1) can be prepared by the routes shown in Schemes 3–5. Compound VIII, where n=2 (Scheme 3), is commercially available from Aldrich Chemical Company, Milwaukee, Wis., USA ("Aldrich"). Compound VIII, where n=1, is known and can be prepared by a method disclosed in the literature. See *Journal of Organic Chemistry*, 1989, 54, pp. 560–569, and references cited therein. Reduction of the acid (VIII) using lithium aluminum hydride in a solvent such as tetrahydrofuran can provide the alcohol (IX). Oxidation of the alcohol using the Swern oxidation conditions or Collin's reagent can provide the aldehyde (X). Reaction of the aldehyde using the Wittig reaction or the Homer Emmons modification of the Wittig reaction and reduction of the resultant double bond using catalytic hydrogenation in a solvent such as ethanol or 2-propanol and a catalyst (Pd/C of Pt/C) provides the ester (XII). The ester can be used directly in the reaction shown in Scheme 1 when Y=nothing. Reduction of the ester using lithium aluminum hydride or borane/dimethyl sulfide in a solvent such as tetrahydrofuran or ether at temperatures between 0°and 80° C. provides the necessary alcohol, XII. Conversion of the alcohol to the mesylate (XIII) (typical conditions may include triethyl amine, methanesulfonyl chloride, methylene chloride or pyridine) or to the halide (XIII) (Carbon tetrabromide or carbon tetrachloride, triphenyl phosphine, methylene chloride) and then conversion to the amine using conditions such as reaction with potassium phthalimide and deprotection of the amine using hydrazine or methyl hydazine can provide the amine (XIV). Compound XIII can be converted to the thiol by converting XXIII to the thiolester (potassium thiolacetate and a solvent such as dimethylformamide) then hydrolysing the thiolester to give the thiol.

Trimethyl quinone can be prepared by a modification of the method described in *Journal of Organic Chemistry*, 54, pp. 728–731 (1989), using 30% hydrogen peroxide (Scheme 4). Reaction of the quinone with a solution formed by adding diethyl methylmalonate to sodium ethoxide provides the ester lactone (XVI). The ester lactone can be reduced using boron trifloride etherate/lithium aluminum hydride or boron trifloride etherate/sodium borohydride to provide the alcohol (XX). See *Journal of Organic Chemistry*, 36pp. 3485–3489 (1971); *Tetrahedron*, 18, pp. 935–958 (1962). The alcohol (XX) can be converted to compounds XXII, XXIII and XXIV using the same standard methods that can be used to convert compound XII to the corresponding amine or thiol.

Since there is an asymmetric carbon in the piperidine ring and in the pyran or pyran ring of the antioxidant moiety, the compounds may occur is a mixture of stereoisomers. The preparation of the individual enantiomeric form may be effected by resolving the alcohols of the formula IX and XVII by forming esters with optionally active carboxylic acids, separating the isomers, and then hydrolyzing the resolved diastereomers. The dihydropyridine compound may be prepared using known methods, such as those described in *Chemical and Pharmaceutics Bulletin*, volume 28, page 2809 (1980).

The compounds of formula (I) and formula (II) may be contained in various types of pharmaceutical compositions, in accordance with formulation techniques known to those skilled in the art. For example, the compounds may be included in tablets, capsules, solutions, suspensions and other dosage forms adapted for oral administration; solutions and suspensions adapted for parenteral use; and suppositories for rectal use. Solutions, suspensions and other dosage forms adapted for topical application to the involved tissues, such as tissue irrigating solutions, are particularly preferred for treatment of acute conditions associated with surgery or other forms of trauma.

The present invention is particularly directed to the provision of ophthalmic compositions adapted for treatment of ophthalmic tissues. The ophthalmic compositions of the present invention will include one or more compounds of formulas (I) or (II) and a pharmaceutically acceptable vehicle for said compound(s). Various types of vehicles may be utilized. The vehicles will generally be aqueous in nature. Aqueous solutions are generally preferred, based on ease of formulation, as well as patient's ability to easily administer such compositions by means of instilling one to two drops of the solutions in the affected eyes. However, the compounds of formulas (I) and (II) may also be readily incorporated into other types of compositions, such as suspensions, viscous or semi-viscous gels or other types of solid or semi-solid compositions. Suspensions may be preferred for compounds of formulas (I) and (II) which are relatively insoluble in water. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Ophthalmic products are typically packaged in multidose form. Preservatives are thus required to prevent microbial contamination during use. Suitable preservatives include: benznlkonium chloride, thimerosal, chiorobutanol, methyl paraben, propyl paraben, phenylethyl alcohol, edetate disodium, sorbic acid, Onamer M, or other agents known to those skilled in the art. Such preservatives are typically employed at a level of from 0.001% to 1.0% by weight.

Some of the compounds of formulas (I) and (II) may have limited solubility in water and therefore may require a surfactant or other appropriate co-solvent in the composition. Such co-solvents include: Polysorbate 20, 60 and 80; Pluronic F-68, F-84 and P-103; cyclodextrin; or other agents known to those skilled in the art. Such co-solvents are typically employed at a level of from 0.01% to 2% by weight.

Viscosity greater than that of simple aqueous solutions may be desirable to inerease ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art. Such agents are typically employed at a level of from 0.01% to 2% by weight.

The pharmaceutical compositions containing one or more compounds of formula (I) and formula (II) may be used to treat patients afflicted with or prone to various types of cellular damage. The concentrations of the compounds in the compositions will depend on various factors, including the nature of the condition to be treated with the compositions. However, the compositions will generally contain one or more of the compounds in a concentration of from about 0.001 to about 5 percent by weight, based on the total weight of the composition ("wt. %").

The route of administration (e.g., topical, parenteral or oral) and the dosage regimen will be determined by skilled clinicians, based on factors such as the exact nature of the condition being treated, the severity of the condition, the age and general physical condition of the patient, and so on.

As indicated above, use of the compounds of formulas (I) and (II) to prevent or reduce damage to ophthalmic tissues at the cellular level is a particularly important aspect of the present invention. Ophthalmic conditions which may be treated include, but are not limited to, cataracts, retinopathies, heredodegenerative diseases, macular degeneration, ocular ischemia, neovascular diseases, glaucoma, and damage associated with injuries to ophthalmic tissues, such as ischemia reperfusion injuries, photochemical injuries, and injuries associated with ocular surgery, particularly injuries to the retina, cornea or other tissues caused by exposure to light or surgical instruments. The compounds may also be used as an adjunct to ophthalmic surgery, such as by vitreal or subconjunctival injection following ophthalmic surgery. The compounds may be used for acute treatment of temporary conditions, or may be administered chronically, especially in the case of degenerative disease. The compounds may also be used prophylactically, especially prior to ocular surgery or noninvasive ophthalmic procedures, or other types of surgery.

The use of physiologically balanced irrigating solutions as pharmaceutical vehicles for the compounds of formula (I) is preferred when the compounds are administered intraocularly. As utilized herein, the term "physiologically balanced irrigating solution" means a solution which is adapted to maintain the physical structure and function of tissues during invasive or noninvasive medical procedures. This type of solution will typically contain electrolytes, such as sodium, potassium, calcium, magnesium and/or chloride; an energy source, such as dextrose; and a buffer to maintain the pH of the solution at or near physiological levels. Various solutions of this type are known (e.g., Lactated Ringers Solution). BSS® Sterile Irrigating Solution and BSS Plus® Sterile Intraocular Irrigating Solution (Alcon Laboratories, Inc., Fort Worth, Tex., USA) are examples of physiologically balanced intraocular irrigating solutions. The latter type of solution is described in U.S. Pat. No. 4,550,022 (Garabedian, et al.), the entire contents of which are hereby incorporated in the present specification by reference.

The doses utilized for any of the above-described purposes will generally be from about 0.01 to about 100 milligrams per kilogram of body weight ("mg/kg"), administered one to four times per day.

The present invention is further illustrated by means of the following examples. Examples 1–8 further illustrate the synthesis of compounds of formulas (I) and (II), and Example 9 further illustrates the pharmaceutical compositions of the present invention.

EXAMPLE 1

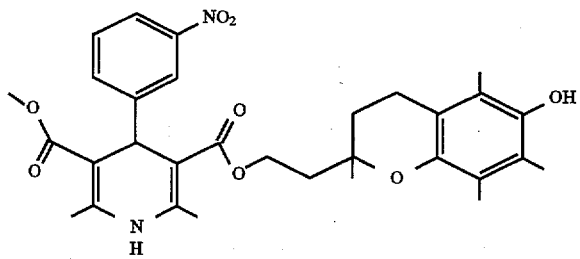

2-[2-(6-hydroxy-2,5,7,8-tetramethylchroman)]ethyl methyl (4R)-2,6-dimethyl-4-(3-nitrophenyl)-1,4-dihydropyridine-3,5-dicarboxylate Thionyl chloride (0.06 mol) is added dropwise to a stirred ice-cooled suspension of (4R)-1,4-dihydro-5-methoxycarbonyl-2,6-dimethyl-4-(3-nitrophenyl)-3-pyridinecarboxylic acid (Chem. Pharm. Bull. volume 37, pages 229–2231, 1989) (0.06 mol) in a mixture of methylene chloride and dimethylformamide (4:1, v/v, 125 mL). The mixture is stirred for 2 h, and 2-[2-(6-hydroxy-2,5,7,8-tetramethylchroman)]ethanol (0.06 mol) in methylene chloride (60 mL) is added dropwise. After the addition is complete the resulting mixture is stirred for 1 h. The reaction is quenched with water (50 mL) and basified with 1N sodium hydroxide. The resulting mixture is extracted with methylene chloride. The combined extracts are washed or with water, dried (MgSO$_4$) and concentrated in vacuo. The residue is purified by chromatography to give the title compound.

EXAMPLE 2

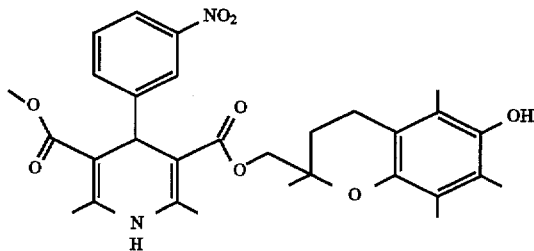

2-[2-(6-hydroxy-2,5,7,8-tetramethylchroman)]methyl (4R)-2,6-dimethyl-4-(3-nitrophenyl)-1,4-dihydropyridine-3,5-dicarboxylate Thionyl chloride (0.06 mol) is added dropwise to a stirred ice-cooled suspension of (4R)-1,4-dihydro-5-methoxycarbonyl-2,6-dimethyl-4-(3-nitrophenyl)-3-pyridinecarboxylic acid (Chem. Pharm. Bull. volume 37, pages 229–2231, 1989) (0.06 mol) in a mixture of methylene chloride and dimethylformamide (4:1, v/v, 125mL). The mixture is stirred for 2 h, and 2-[2-(6-hydroxy-2,5,7,8-tetramethylchroman)]methanol (0.06 mol) in methylene chloride (60 mL) is added dropwise. After the addition is complete the resulting mixture is stirred for 1 h. The reaction is quenched with water (50 mL) and basified with 1N sodium hydroxide. The resulting mixture is extracted with methylene chloride. The combined extracts are washed with water, dried (MgSO$_4$) and concentrated in vacuo. The residue is purified by chromatography to give the rifle compound.

EXAMPLE 3

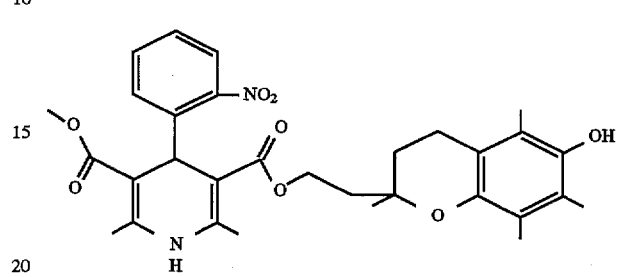

2-[2-(6-hydroxy-2,5,7,8-tetramethylchroman)]ethyl methyl2,6-dimethyl-4-(2-nitrophenyl)-1,4-dihydropyridine-3,5-dicarboxylate Diketene (32 mmol) is added dropwise to a stirring suspension of 2-[2-(6-hydroxy-2,5,7,8-tetratnethylchroman)]ethanol(8.0 mmol) in toluene (40 mL) warmed at 80° C. After stirring for 18 h at 80° C., the reaction mixture is concentrated in vacuo and the residue is purified by chromatography. A solution of the 2-[2-(6-hydroxy-2,5,7,8-tetrarnethylchroman)]ethyl 3-oxobutyrate(4.31 mmol),2-nitrobenzaldehyde (4.31 mmol) and methyl aminocrontonate (4.31 mmol) in 2-propanol is warmed at reflux for 16 h. The reaction mixture is cooled to ambient temperature and concentrated in vacuo. The residue is purified by chromatography to give the title compound.

EXAMPLE 4

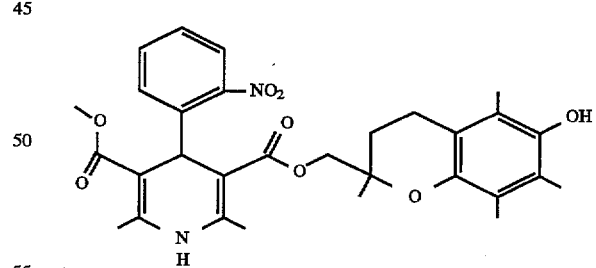

2-[2-(6-hydroxy-2,5,7,8-tetramethylchroman)]methyl methyl 2.6-dimethyl-4-(2-nitrophenyl)-1,4dihydropyridine-3,5-dicarboxylate Following the procedure of example 3, the title compound is prepared by substituting 2-[2-(6-hydroxy-2,5,7,8-tetramethylchroman)]methanol for 2-[2-(6-hydroxy-2,5,7,8-tetramethyl-chroman)]ethanol.

EXAMPLE 5

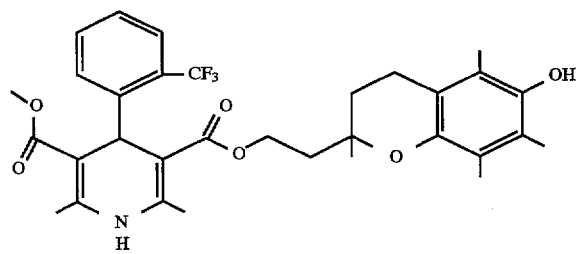

2-[2-(6-hydroxy-2,5,7,8-tetramethylchroman)]ethyl
methyl 2,6-4-(2-trifluoromethyl-phenyl)-1,4-
dihydropyridine-3,5-dicarboxylate Following the procedure of example 3, the rifle compound is prepared by substituting 2-(trifluoromethyl)benzaldehyde for 2-nitrobenzaldehyde.

EXAMPLE 6

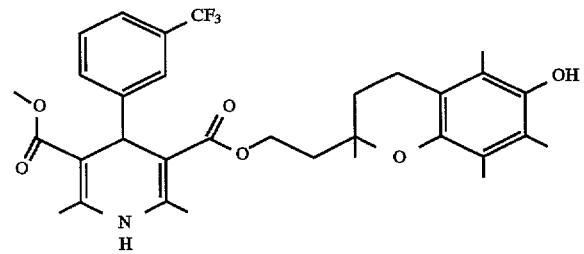

2-[2-(6-hydroxy-2,5,7,8-tetramethylchroman)]ethyl
methyl2,6-dimethyl-4-(3-trifluoromethyl-phenyl)-1,
4-dihydropyridine-3,5-dicarboxylate Following the procedure of example 3, the rifle compound is prepared by substituting 3-(trifluoromethyl)benzaldehyde for 2-nitrobenzaldehyde.

EXAMPLE 7

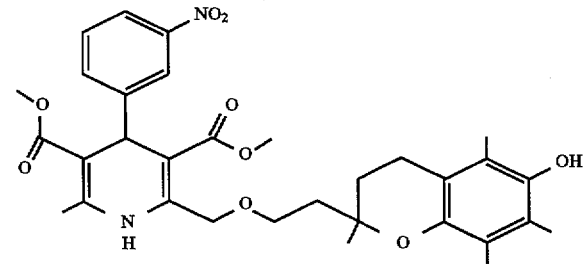

Dimethyl2-[2-[2-(6-hydroxy-2,5,7,8-
tetramethylchroman)]ethoxy]methyl-6-methyl-4-(3-
nitro-phenyl)-1,4-(dihydropyridine-3,5-dicarboxylate A solution of 2-[2-(6-hydroxy-2,5,7,8-tetramethylchroman)]ethanol (0.10 mol) in tetrahydrofuran (50 mL) is added dropwise to a stirred suspension of sodium hydride (50% oil dispersion, 0.24 mol) in 50 mL of tetrahydrofuran. After the addition is complete, the mixture is stirred for 1 h and then was cooled in an ice-water bath. Methyl 4-chloroacetoacetate (0.14 mol) in tetrahydrofuran (50 mL) is added dropwise and the reaction mixture was allowed to come to ambient temperature. After stirring at ambient temperature for 18 h, the reaction mixture is added to ice-water (100 mL) and concentrated hydrochloric acid (2 mL). The resulting mixture is extracted with ethyl acetate and the combined extracts dried (MgSO₄), and concentrated in vacuo. The product is purified by chromatography to provide the title compound.

A mixture of methyl 4-[2-(6-hydroxy-2,5,7,8-tetramethylchroman)ethoxy]acetoacetate (0.15 mol) and 3-nitrobenzaldehyde (0.09 mol) in ethanol (40 mL) is warmed at reflux for 15 min. Methyl 3-aminocrotonate (0.087 mol) and acetic acid (5 mL) are added and the resulting mixture is warmed at reflux for 16 h. The reaction mixture is cooled to ambient temperature and concentrated in vacuo. The residue is dissolved in methylene chloride and washed with water, dried and concentrated in vacuo. The residue is purified by chromatography to give the title compound.

EXAMPLE 8

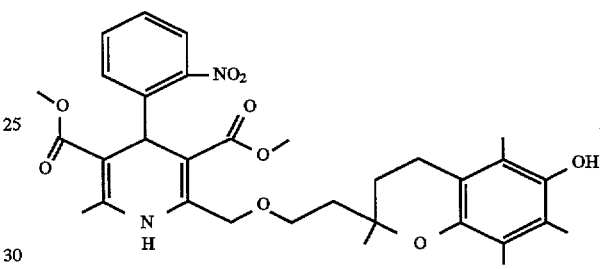

Dimethyl2[2[2(6-hydroxy-2,5,7,8-
tetramethylchroman) ethoxy]methyl]-6-methyl-4-(2-
nitrop-phenyl)-1,4-dihydropyridine-3,5-
dicarboxylate Following the procedure of example 7, the title compound is prepared by substituting 2-nitrobenzaldehyde for 3-nitrobenzaldehyde.

The following example is provided to further illustrate the pharmaceutical compositions of the present invention, particularly compositions intended for topical application to the eye. In this example, the term "Compound" is intended to represent any of the compounds of formula (I) and formula (II) above.

EXAMPLE 9

| Ingredient | Amount (wt. %) | Purpose |
|---|---|---|
| Compound (free base) | 1.0 | Active ingredient |
| Polyvinyl alcohol, USP | 1.4 | Excipient |
| Monobasic sodium phosphate (Monohydrate), USP | 0.05 | Buffering agent |
| Dibasic Sodium Phosphate (Anhydrous), USP | 0.15 | Buffering agent |
| Sodium chloride, USP | 0.5 | Tonicity agent |
| Disodium EDTA (Edetate disodium), USP | 0.01 | Preservative |
| Polysorbate 80, NF | 0.05 | Surfactant |
| Benzalkonium chloride solution, NF | 0.01 + 5 excess | Preservative |
| Sodium hydroxide, NF | q.s. | pH adjustment |
| Hydrochloric acid, NF | q.s. | pH adjustment |
| Water for injection, USP | q.s. | Vehicle |

What is claimed is:

1. A method of preventing or alleviating damage to mammalian ophthalmic tissues which comprises administering to a mammal a therapeutically effective amount of a composition comprising an amount of a compound of the following formula effective to decrease free radical or oxidative damage and control intracellular free calcium levels in said tissues:

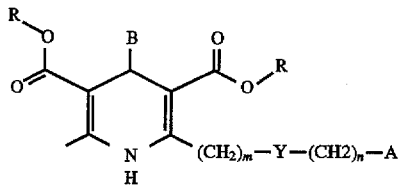
(I)

and

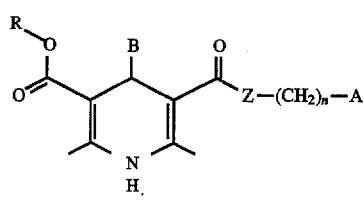
(II)

wherein:

A is an antioxidant selected from the group consisting of:

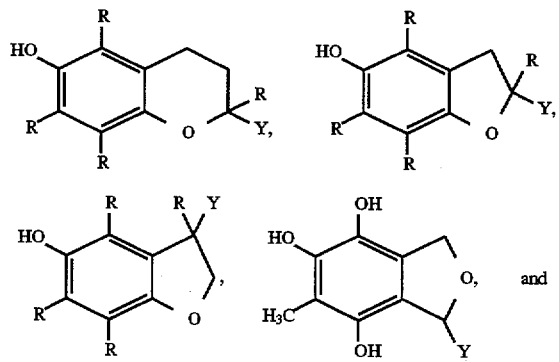

and

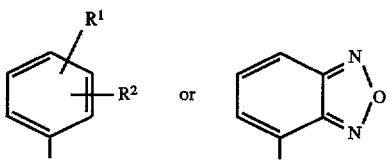

R is $C_1$ to $C_6$ alkyl;
n is a whole number of from 1 to 6;
m is a whole number of from 1 to 6;
Z is O or NH;
Y, if present, is O or $S(O)_{n'}$, wherein n' is 0, 1 or 2; and
B is:

wherein:
$R^1$ and $R^2$ are the same or different and are selected from H,I,Br,Cl,F,$CF_3$,CN, $NO_2$ and $S(O)_n$, and a pharmaceutically acceptable vehicle therefor.

2. A method according to claim 1, wherein the composition is administered to a human patient.

3. A method according to claim 1, wherein the composition is topically applied to ophthalmic tissues.

4. A method according to claim 3, wherein the pharmaceutically acceptable vehicle comprises a physiologically balanced irrigating solution.

5. A method according to claim 4, wherein the composition is administered to the patient in conjunction with an ophthalmic surgical procedure.

* * * * *